US005869456A

United States Patent [19]
Levy et al.

[11] Patent Number: 5,869,456
[45] Date of Patent: Feb. 9, 1999

[54] USE OF GLUTATHIONE DIESTERS

[75] Inventors: Ellen Levy, Brooklyn; Mary Anderson; Alton Meister, both of New York, all of N.Y.

[73] Assignee: Cornell Research Foundation, Inc., Ithaca, N.Y.

[21] Appl. No.: 417,909

[22] Filed: Apr. 6, 1995

Related U.S. Application Data

[63] Continuation of Ser. No. 56,499, May 3, 1993.

[51] Int. Cl.$^6$ .................................................. A61K 38/00
[52] U.S. Cl. .............................................. 514/19; 514/19
[58] Field of Search ........................ 514/18, 19; 530/331; 560/147

[56] References Cited

U.S. PATENT DOCUMENTS

| | | | |
|---|---|---|---|
| 2,209,299 | 7/1940 | Schoeller et al. | 530/332 |
| 2,250,553 | 7/1941 | Ruskin | 514/18 |
| 2,376,186 | 5/1945 | Rapkine | 530/332 |
| 2,702,799 | 2/1955 | Laufer | 530/332 |
| 2,711,989 | 6/1955 | Laufer et al. | 435/71.1 |
| 2,760,956 | 8/1956 | Brick | 530/332 |
| 2,900,376 | 8/1959 | Amiard et al. | 568/13 |
| 2,938,023 | 5/1960 | Weygand et al. | 530/332 |
| 3,482,025 | 12/1969 | Murakami et al. | 514/419 |
| 3,741,948 | 6/1973 | Murakami et al. | 530/337 |
| 3,882,097 | 5/1975 | Pfister et al. | 530/332 |
| 3,950,387 | 4/1976 | Joullie et al. | 560/16 |
| 3,984,569 | 10/1976 | Kalopissis et al. | 514/562 |
| 4,643,990 | 2/1987 | Umehara et al. | 514/18 |
| 4,709,013 | 11/1987 | Nagano | 530/332 |
| 4,710,489 | 12/1987 | Meister | 514/18 |
| 4,784,685 | 11/1988 | Meister | 71/106 |
| 4,879,370 | 11/1989 | Meister | 530/331 |
| 4,927,808 | 5/1990 | Kitahara et al. | 514/19 |
| 4,968,671 | 11/1990 | Asano et al. | 514/18 |

FOREIGN PATENT DOCUMENTS

| | | |
|---|---|---|
| 249401 | 12/1987 | European Pat. Off. . |
| 257992 | 3/1988 | European Pat. Off. . |
| 20166 | 8/1968 | Japan . |

OTHER PUBLICATIONS

Vos, O., et al, Int. J. Radiat. Biol., vol. 53, No. 2, 273–281 (1988).
Levy, E., et al, 1991 Faseb Abstract Form, Glutathione Derivatives: Transport and Utilization.
Levy, E., et al, Proc. Natl. Acad. Sci. USA, vol. 90, pp. 9171–9175 (Oct. 1993).
Meister, A., et al, Ann. Rev. Biochem., 52: 711–760 (1983).
Meister, A., Metabolism and Function of Glutathione, from coenzymes and Cofactors, vol. III, Glutathione Chemical, Biochemical and Medical Aspects, Part A, Dolphin, D., et al, eds., pp. 367–474, John Wiley & Sons, Inc., 1989.
Meister, A., Science, vol. 220, 472–477 (Apr. 1983).
Meister, A., Hepatology, vol. 4, No. 4, pp. 739–742 (1984).
Wellner, V.P., et al, Proc. Natl. Acad. Sci. USA, vol. 81, 4732–4735 (Aug.1984).
Puri, R. N., et al, Proc. Natl. Acad. Sci. USA, vol. 80, 3343–3347 (May 1990).
Suthanthiran, M., et al, Proc. Natl. Acad. Sci. USA, vol. 87, 3343–3347 (May 1990).
Vos, O., et al, Chem. Abst. 108: 164136y (1988).
Thornalley, P. K., Chem. Abst. 115:9306e (1991).

*Primary Examiner*—Samuel Barts
*Attorney, Agent, or Firm*—Pennie & Edmonds LLP

[57] ABSTRACT

This invention relates to substantially pure diloweralkyl esters of glutathione and the use of these components to increase intracellular levels of glutathione.

8 Claims, No Drawings

USE OF GLUTATHIONE DIESTERS

This is a continuation of co-pending application Ser. No. 08/056,499 filed on May 3, 1995.

This invention was made with Government support under Grant Nos. AM-12034 and AI-31804, awarded by the National Institutes of Health. The Government has certain rights in the invention.

DESCRIPTION OF THE PRIOR ART

It is well-known that the tripeptide thiol glutathione (L-γ-glutamyl-L-cysteinyl-glycine; (GSH) found in virtually all cells functions in metabolism, transport and cellular protection. Glutathione functions in the reduction of the disulfide linkages of proteins and other molecules, in the synthesis of the deoxyribonucleotide precursors of DNA, and in the protection of cells against the effects of free radicals and of reactive oxygen intermediates such as peroxides that are formed in metabolism.

Modifications of glutathione metabolism may be achieved by administration of selective enzyme inhibitors to decrease intracellular glutathione levels, or by providing compounds that increase glutathione synthesis. Such effects are useful in chemotherapy and radiation therapy and in protecting cells against the toxic effects of drugs, other foreign compounds and oxygen. Indeed, the diverse functions of GSH are relevant to many fields of biology, including not only enzymology and transport but also pharmacology, radiation biology, cancer therapy, toxicology, endocrinology, microbiology and agriculture. The enzymatic and transport phenomena of glutathione metabolism are outlined in Meister. "Selective Modification Of Glutathione Metabolism", *Science*, Volume 220, Number 4596, 472–477 (April 1983), which is hereby incorporated by reference.

Modification of glutathione metabolism to deplete or increase cellular GSH may serve various purposes. For instance, it has long been known that thiols protect cells against the effects of irradiation. Since decreasing cellular GSH makes cells more susceptible to irradiation, glutathione depletion is useful in chemotherapeutic situations in which the cells to be killed and the cells to be spared have substantially different quantitative requirements for GSH. Depletion of GSH by inhibition of its synthesis also serves as a valuable adjuvant in chemotherapy with drugs that are detoxified by reactions involving GSH.

Conversely, development of resistance to a drug or to radiation may be associated with an increase in cellular GSH. GSH serves effectively in the detoxification of many drugs; for example, it is known that a significant pathway of acetaminophen detoxification involves conjugation with GSH.

Treatment with a thiazolidine such as L-2-oxothiazolidine-4-carboxylic acid, may be of value to patients with liver disease and to premature infants who may be deficient in the utilization of methionine sulfur for cysteine formation, and thus in GSH synthesis. The effectiveness of such a thiazolidine as an intracellular cysteine precursor depends on the presence of 5-oxoprolinase, an enzyme activity found in almost all animal cells. This enzyme also occurs in plants, suggesting that such a thiazolidine, and hence glutathione, may be useful as a safener in agriculture to protect crop plants against the toxic effects of herbicides.

Various methods are known to increase cellular levels of glutathione. Glutathione is composed of three amino acids: glutamic acid, cysteine, and glycine. Administration to animals of the amino acid precursors of glutathione may produce an increase in cellular glutathione, but there is a limit to the effectiveness of this procedure. Cellular concentrations of GSH are dependent on the supply of cysteine, which is often the limiting amino acid, and which is derived from dietary protein and also by trans-sulfuration from methionine in the liver. However, administration of cysteine is not an ideal way to increase GSH concentrations because cysteine is rapidly metabolized and furthermore, it is very toxic. Administration to animals of compounds that are transported into cells and converted intracellularly into cysteine is sometimes useful in increasing cellular glutathione levels. For example, thiazolidine L-2-oxothiazolidine-4-carboxylate is transported into cells, where it is converted by 5-oxoprolinase to L-cysteine, which is rapidly used for GSH synthesis.

Another way in which tissue GSH concentration may be increased is by administration of γ-glutamylcysteine or of γ-glutamylcystine. The administered γ-glutamyl amino acid is transported intact and serves as a substrate of GSH synthetase. It is also known that administration of N-acetyl-L-cysteine can often increase tissue concentrations of GSH.

That the administration of glutathione itself might lead to increased glutathione levels has also been considered. However, there is no published evidence that shows that intact glutathione enters cells. In fact, there are several reports on particular biological systems indicating that glutathione itself is not transported into cells. The increase in cellular glutathione sometimes found after administration of glutathione is due to (a) extracellular breakdown of glutathione, (b) transport into cells of free amino acids or dipeptides derived from glutathione extracellularly, and (c) intracellular resynthesis of glutathione.

These previous methods of increasing intracellular glutathione concentration are disadvantageous in the areas of efficiency, toxicity, limits on effective concentration obtainable, etc. as discussed heretofore. In addition, the known methods which depend on synthesis of GSH by increasing the supply of substrates to the two synthetases involved, depend on the presence of the synthetases, the first of which is subject to feedback inhibition by GSH.

It is well-known that certain glutathione monoestors are an effective glutathione delivery system; see for example U.S. Pat. Nos. 4,710,489; 4,784,685 and 4,879,370.

The esters of glutathione are typically administered by injection after dissolution in water. However, the esters are also effective after oral administration. The esters can be admixed with suitable pharmaceutically acceptable carriers such as the aforementioned water or physiological saline solution in the preparation of liquid formulations or with lactose, sucrose, starch, talc or the like in formulating powders.

It was originally found, and reported in the above-identified three patents that diesters of glutathione were toxic to mice and thereof not further explored as to possible utility. The exact reason for the apparent toxicity is not known, but it is strongly suspected that an impurity caused the toxicity. It has now been found that the diesters, have utility and are not in fact toxic.

Thus, in summary it appears known that glutathione is not effectively transported into animal cells, but that previous studies have shown that monoesters of GSH in which the glycine carboxyl group is esterified are highly efficient delivery agents for GSH. Thus, the monoglycyl ethyl ester of GSH is well transported into many animal tissues (e.g., liver, kidney, pancreas, spleen, heart, lung, skeletal muscle, lymphocytes), and hydrolyzed intracellularly to form GSH. GSH mono esters are more effective than GSH and various other GSH derivatives in increasing cellular GSH levels.

DESCRIPTION OF THE INVENTION

Experiments by the inventors in which suspensions of human erythrocytes were incubated with various preparations of GSH mono esters showed that metal ion (Cu, Fe) contamination leads to a marked decrease in the levels of cellular thiols. In these studies it was observed that certain GSH mono ethyl ester preparations that contained about 10–15% of the corresponding diester were unexpectedly very effective in increasing cellular GSH levels. This observation led to the re-examination of GSH diethyl ester, which had not previously been tested with erythrocytes, as a potential cellular GSH delivery compound. It has now been found that GSH diethyl ester is very effectively transported into human erythrocytes and also into certain other cells. An improved method for preparing this compound in high purity has been devised. Earlier evidence suggested that GSH dimethyl ester may be toxic to mice, but toxicity was not observed in the present studies in which GSH diethyl ester was given to mice and to hamsters. GSH diethyl ester is rapidly converted to GSH mono (glycyl) ester by esterase activity present in rat and mouse blood plasma. This limits the usefulness of GSH diethyl ester as a GSH delivery agent in these species; indeed, we observed that injection of GSH diethyl ester and of GSH mono ester into mice gives similar results. However, we have found that human blood plasma does not have detectable GSH diester α-esterase activity. Thus, GSH diethyl ester would be relatively stable in human plasma and might serve as an efficient cellular GSH delivery agent because of its expected increased permeability into cells. In the present work it was found that GSH diethyl ester is more effectively transported than GSH mono ethyl ester into human erythrocytes and leukocytes (including T-lymphoctyes). Study of blood plasma obtained from several species showed that hamster plasma, like human, lacks detectable GSH diester α-esterase activity, suggesting that the hamster might serve as a useful animal model for further study of GSH diester metabolism. Plasma from certain larger animals (guinea pig, rabbit, sheep) also lack this esterase.

The present invention is directed in part to a method for increasing intracellular glutathione levels by administering an alkyl diester of glutathione. Such esters are transported into, for example, liver and kidney cells, and are de-esterified within the cells, thus leading to increased cellular levels of glutathione.

In particular it has been found that glutathione diethyl ester (GSH-DE) is very effectively transported into human erythrocytes (RBC). It previously had been found that glutathione mono ethyl ester (GSH-ME) is transported into RBC, but now the inventors find that GSH-DE is much more effective.

As shown in Table 1, GSH-ME gives total RBC thiol levels of about 3 mM (about twice the control, i.e., the normal thiol [GSH] that is there). On the other hand, after suspending RBC in solutions containing GSH-DE, one sees total thiol levels of about 20 mM. Much of this 20 mM total is accounted for as GSH-ME. Thus, the RBC splits (intracellularly) the α-ester bond of GSH-DE to form GSH-ME. Increase of thiols is found in erythiocytes (tables 1 and 2) as well as in Leukocytes (table 3). In rats and mice— animals commonly used in laboratory experiments—GSH-DE is split rapidly to GSH-ME in the blood plasma so there is no advantage of giving GSH-DE over giving GSH-ME. However, human plasma (and as was subsequently found, hamster plasma) lacks significant α-esterase activity, and thus GSH-DE is not split to GSH-ME in plasma. GSH-DE is therefore available for use in humans (and in the hamster laboratory animal model) for potential uptake into cells of different tissues.

Another advantage of GSH-DE in humans is that this compound readily enters into peripheral leukocytes including T-lymphocytes.

When whole blood from human donors is incubated with GSH-DE, both the RBC and the leukocytes (WBC) develop high levels of thiol.

Further, there is now good evidence that the disease, Acquired Immuno Deficiency Syndrome (AIDS) is associated with GSH deficiency, especially in lymphocytes, the class of WBC (white blood cells) that includes those damaged by the AIDS virus. Experimental trials in patients are now in progress with compounds that increase GSH levels, such as 2-oxothiazolidine-4-carboxylate and N-acetyl cysteine. It has previously been suggested that GSH-ME might be used in treatment of AIDS. The present findings suggest that GSH-DE might be even better.

Table 4 shows some results on human PBM (PBM includes lymphocytes) on total thiols with GSH-ME [10.6 mM in 90 min] and with GSH-DE [33 mM in 90 min]. Data are given in Table 5 on T-cells.

Data on the model animal (hamster)—Table 6—show that GSH-DE is more effective than GSH-ME in raising GSH levels in liver.

GSH-DE is more hydrophobic than GSH-ME and might therefore be expected to be very well transported across the lipid-containing cell membrane. GSH-DE, in contrast to GSH-ME, has a net positive charge, and would therefore be expected to be attracted to negatively charged cellular components (e.g., DNA). This could potentially help to protect DNA against damage of various types.

Previous ideas and statements on the potentially beneficial effects of increasing cellular GSH apply to GSH-DE as well. GSH-DE seems to have greater potential for being transported into some cells than GSH-ME. Although it had previously been thought that GSH-DE would be readily split extracellularly to GSH-ME—and would therefore be essentially equivalent to GSH-ME—it now appears that GSH-DE is not split extracellularly in human plasma. Therefore, GSH-DE is a good prospect for human use. It gets into cells easily, and it increases cellular thiol levels.

By the present method involving administration of GSH diesters, increased levels of GSH are provided in an efficient, rapid manner. In addition, the present invention provides the pure dialkyl esters, and a method to produce them as disclosed hereinafter.

By the present method, esterified glutathione is transported intact into the cell, where it is de-esterified, thus leading to increased cellular levels of glutathione. Glutathione has two carboxyl groups, one on the glutamic acid residue and one on the glycine residue. The compounds used in the present method are dialkyl esters of glutathione in which both carboxyl groups are esterified. Thus, the compounds used in the present invention have the structure:

wherein R and $R_1$ are each independently an alkyl group containing 1 to 10 carbon atoms. Pharmaceutically acceptable salts of the above compounds are within the scope of the present invention.

The alkyl groups of the GSH dialkyl ester according to the invention are saturated, straight or branched, alkyl groups of 1 to 10 carbon atoms and include preferably a saturated straight alkyl group such as methyl, ethyl, propyl, butyl, pentyl, hexl, heptyl, octyl, nonyl or decyl and a saturated branched alkyl group such as isopropyl isobutyl, sec-butyl, tert-butyl or isopentyl. Among them, methyl, ethyl, and isopropyl are especially suitable for medical use.

The source of glutathione used in the present invention is not important, and thus glutathione may be synthesized or isolated by methods conventional in the art or purchased.

The esterification method preferred is described below. While this method is presently preferred, any method of preparation can be used provided the final compound is at least 95% and preferably at least 99% pure and is substantially free of impurities which are more toxic to animals than the compound itself.

The diesters of glutathione are typically administered by injection after dissolution in water. However, the diesters are also effective after oral administration. The diesters can be admixed with suitable pharmaceutically acceptable carriers such as the aforementioned water or physiological saline solution in the preparation of liquid formulations or with amino acid mixtures, vitamins, lactose, sucrose, starch, talc or the like in formulating powders.

A suitable therapeutically effective dosage can be selected based on routine experimentation, particularly in view of prior art uses for glutathione and monoesters of glutathione an the examples hereinafter, bearing in mind the approximately stoichiometric intracellular, hydrolysis believed to occur. In any event, one can monitor glutathione level in the patient or use other parameters of effectiveness depending on the nature of the toxicity being treated. At this time, a suggested dosage is about 0.1 to 10 millimoles of ester per kg of body weight, preferably about 1 to 3 millimoles of ester per kg of body weight, one to six times a day.

Administration is carried out to typically result in intracellular levels of glutathione of 0.5 to 3 millimolar within 0.5 to 2 hours after administration.

Although the precise mechanism of the reaction is not known, the increase in intracellular glutathione obtained by the present method is interpreted to indicate that the administered glutathione ester is transported into the cells of at least the liver and kidney where it is hydrolyzed to glutathione. Such hydrolysis has been demonstrated in in vitro experiments in which glutathione diesters were incubated with homogenates of liver and kidney.

EXAMPLES
MATERIALS AND METHODS

GSH was obtained from Calbiochem, Sigma or U.S. Biochemical Corporation. Monobromobimane was obtained from Calbiochem or Molecular Probes, Inc. (Eugene, Oreg.). DTT was obtained from Sigma. HCl gas was obtained from Matheson Gas Products (E. Rutherford, N.J.). $H_2SO_4$ and anhydrous diethyl ether were obtained from Mallinckrodt. Chelex-100 (200–400 mesh, $Na^+$ form) and AG1-X2 (200–400 mesh, $Cl^-$ form) resins were obtained from Bio-Rad. PBS was obtained from GIBCO. Male Syrian hamsters (50–60 g) were from Charles River (Canada). Male Swiss Webster mice (21–25 g) were from Tacoroic Farms. Blood from other species was kindly provided by the Laboratory of Animal Medicine at Cornell University Medical College.

Glutathione monoethyl ester (GSH-ME). GSH-MEHCL and GSH-ME free base were prepared as described (4,5).

Glutathione Diethyl Ester (GSH-ME). GSH (5 g) was suspended at 0° in a solution prepared by adding 5.6 ml of concentrated $H_2SO_4$ to 100 ml of ethanol, and the slurry was stirred briefly at 0° C. to effect complete solution. The reaction goes to about 70% of completion after standing at 0° C. for 4–7 days. After adding 10 vols of diethyl ether and standing at 0° C. for several hours, the ether was decanted and the syrup was dried under a stream of dry nitrogen.

The syrup was dissolved in the minimal amount of cold water and carefully adjusted to pH 4–5 with 10M NaOH. This solution was applied to a Chelex column ($Na^+$ form, buffered at pH 5.5) and then eluted with $H_2O$. The fractions were monitored with DTNB. After complete elution of the monoethyl ester, the mobile phase was changed to 0.2M $Na_2SO_4$, which eluted the diester. The diester solution was lyophilized and the solid was extracted with absolute ethanol until the extracts were thiol-free. The combined ethanolic solutions were evaporated to a small volume under vacuum and the diester was precipitated by adding ether. The white solid obtained was repeatedly washed with ether, dried under a stream of $N_2$, and then placed under vacuum over KOH.

Mass Spectroscopy. FAB(+) spectrum shows the molecular ion at 364 amu $(M+H^+)$. $^1H$ NMR (300 $MH_z$) in $D_2O$: 2 overlapping triplets at 1.22 and 1.32 ppm (6 protons), ethyl-$CH_3$ groups; multiplet, 2.25 ppm (2 protons), γ-glutamyl β-$CH_2$; multiplet, 2.61 ppm (2 protons), γ-glutamyl γ-$CH_2$; multiplet, 2.95 ppm (2 protons), cysteinyl β-$CH_2$; AB quartet, 4.02 ppm (2 protons), glycincyl —$CH_2$; unresolved multiplet centered at 4.25 ppm (5 protons), ethyl —$CH_2$ and γ-glutamyl α-CH; triplet 4.56 ppm (1 proton); cysteinyl α-CH. Spectrum referenced to TSP.

Analysis of Erythrocyte Thiol by DTNB. Cell supernatant (40 μl) was added to 1 ml of 6 mM DTNB (in 143 mM phosphate buffer, pH 7.5, containing 6.3 mM EDTA). The change in absorbance at 412 nm after 1 min was converted to a value for total thiol using a GSH standard curve. The GSH standard were prepared in a 1:2:2 mixture of PBS: 0.435M acetic acid: 10% SSA (containing 2 mM EDTA) ("RBC Mix").

Derivatization of Cell Thiols for HPLC Analysis. Derivatization mixtures are as follows: Erythrocyte Lysates: 155 μl 50 mM DTPA (pH 7), 110 μl 3.33% SSA, total 180 μl cell supernatant plus "RBC Mix", 10 μl 0.1M mBBr (in $CH_3CN$), 100 μl of 2M Tris·HCl (pH 9 at room temperature). The samples were placed in the dark for 20–30 minutes at room temperature; the reaction was quenched with 90 μl of glacial acetic acid. Reduced Erythocyte Lysates. 155 μl mM DTT in 50 mM DTPA (pH 7), SSA, sample, and "RBC Mix" as above Tris was added and the samples were agitated at room temperature for 25 min. 20 μl Tris and 10 μl mBBr were added; the derivatization proceeds as above.

T Cell and PBM Lysates: 120 μl 4 mM DTPA, total 360 μl sample/4.31% SSA (containing 0.5 mM DTPA), 100 μl Tris, 5μ mBBr; 20 min. in the dark, 15 μl glacial acetic acid.

Plasma Samples: 190 μl 50 mM DTPA, total 70 μl sample plus 3.33% SSA, 17.5 μl Tris, 10 μl of mBBr; after 20 min in the dark, 7.5 μl glacial acetic acid. Reduced Plasma Samples: 170μ 50 mM DTPA, 20 μl 16 mM DTT in 50 mM DTPA, remainder as above; the samples were agitated at room temperature for 20 min. After reduction, mBBr was added and the derivatization proceeds as above.

Other Animal Tissues. 385 μl 50 mM DTPA, 140 μl sample. 20 μl mBBr, 40 μl Tris; 20 minutes in the dark, 15 μl glacial acetic acid. Standards for all sample types were prepared using identical derivatization procedures.

HPLC Analysis of Cellular Thiols. Samples were chromatographed on an Altex Ultrasphere ODS reverse phase column (5μ; 4.6 mm×25 cm), using one of three gradients: (1) Buffer A: 12.8% MeOH, 0.25% acetic acid, 87.75% $H_2O$, pH 3.9. (2) Buffer B: 90.0% MeOH, 0.25% acetic acid, 9.75% $H_2O$ (no pH Adjustment). (3) Gradient 1: Initial, 100% A, linear gradient to 50% B at 25 min., linear gradient to 100% B at 35 min., wash with 100% B to 39.5 min.; step to 100% A at 40 min.; equilibration with 100% A to 48 min. Gradient 2: Initial, 100% A, linear gradient to 75% B at 25 min., remainder identical to Gradient 1. Gradient 3: Initial, 100% A, linear gradient to 65% A, 35% B at 25 minutes, remainder identical to gradient 1. Flow rates were 1 ml/min.

Recovery of Tissues from Syrian Hamsters. Animals were anesthetized by i.p. administration of xylazine and ketamine, decapitated, and exsanguinated. Blood was mixed with 50 μl EDTA (0.5M, pH 7). Plasma was recovered by centrifugation; one-half vol. 10% SSA/0.5 mM DTPA was added. Liver: one lobe was removed, rinsed with $H_2O$, blotted, weighed, and homogenized in 5% SSA (0.5 Mm DTPA) (5 vol/g tissue). Kidney: one kidney was removed and decapsulated and then processed as with liver. Brain: processed as liver.

Atomic Absorption Analysis. Atomic absorption analysis was kindly performed by the Trace Metal Analysis Center of the Hospital for Special Surgery.

NMR and Mass Spectroscopy. NMR and mass spectroscopy were performed at the Rockefeller University.

TABLE 1

Thiol Levels After Treatment of Human Erythrocytes with GSH Esters*

| Exp. No. | Thiol Applied | Thiol Found | Thiol Levels (mM) | | |
|---|---|---|---|---|---|
| | | | 7 min | 45 min | 90 min |
| 1. | None (saline) | GSH | 1.66 ± 0.29 | 1.64 ± 0.35 | 1.54 ± 0.15 |
| 2. | GSH | GSH | 1.91 ± 0.05 | 2.04 ± 0.06 | 1.83 ± 0.07 |
| 3. | GSH-ME | GSH | 1.72 ± 0.27 | 1.83 ± 0.31 | 1.90 ± 0.30 |
| | | GSH-ME | 0.932 ± 0.04 | 1.66 ± 0.04 | 1.67 ± 0.08 |
| | | Total | 2.65 ± 0.31 | 3.49 ± 0.35 | 3.57 ± 0.38 |
| 4. | GSH-DE | GSH | 1.74 ± 0.22 | 1.77 ± 0.22 | 2.02 ± 0.30 |
| | | GSH-ME | 4.01 ± 0.41 | 9.15 ± 0.49 | 14.6 ± 1.2 |
| | | GSH-DE** | 4.19 ± 1.47 | 3.61 ± 1.29 | 3.51 ± 1.28 |
| | | Total | 9.99 ± 2.10 | 14.5 ± 2.0 | 20.1 ± 2.8 |

*Each determination was done in triplicate. The values given are means ± S.D. for data on 2 donors, except for exp. 2; the control (exp. 1) values for this donor were 1.94 ± 0.01 (7 min), 1.97 ± 0.12 (45 min) and 1.67 ± 0.09 (90 min).
**Triplicate and quadruplicate determinations.

Whole blood was collected with EDTA or DTPA (0.5M, pH 7) as anticoagulant (0.4 ml/8–12 ml blood). Plasma and buffy coat were removed after centrifugation and the erythrocytes washed 3 times with 1–2 vol PBS/5 mM DTPA or EDTA. Packed erythrocytes were suspended in one-half vol. PBS. To each suspension was one-third vol. GSH, GSH-ME or GSH-DE (80 mM, pH 7). After incubation at 37° C. for the indicated times, aliquots were removed, washed (3–4×) with PBS/EDTA/DTPA, lysed with one volume 0.435M acetic acid, protein-precipitated with one volume 10% SSA/2 mM DTPA, and centrifuged to remove cell debris. Supernatants were derivatized for HPLC analysis as described in Materials and Methods.

TABLE 2

Thiol Levels of Human Erythrocytes After Treatment of Whole Blood with GSH Esters*
Thiol Levels Found (mM)

| Thiol Applied | GSH | GSH-ME | GSH-DE | Total |
|---|---|---|---|---|
| None (saline) | 2.08 ± 0.32 | | | 2.08 ± 0.32 |
| GSH | 2.12 ± 0.47 | | | 2.12 ± 0.47 |
| GSH-ME | 2.35 ± 0.52 | 3.45 ± 0.73 | | 5.80 ± 1.25 |
| GSH-DE | 2.24 ± 0.45 | 6.26 ± 0.50 | 8.61 ± 0.31 | 17.1 ± 1.24 |

*Values are means ± S.D. of seven total determinations (3 separate donors).

Whole blood (see Table 1) was mixed with one-half volume of 120 mM GSH, GSH-ME, or GSH-DE at pH 7. The samples were incubated for 30 minutes at 37° C. and then centrifuged. After removal of plasma and buffy coat, the erythrocytes were washed and processed as described in Table 1.

TABLE 3

Thiol Levels in Human Peripheral Blood Mononuclear Cells After Treatment of Whole Blood with GSH Esters*
Thiol Levels Found (nmol/$10^6$ cells)

| Thiol Applied | GSH | GSH-ME | GSH-DE | Total |
|---|---|---|---|---|
| None (saline) | 0.871 | | | 0.871 |
| GSH-ME | 1.46 | 2.08 | | 3.54 |
| GSH-DE | 4.24 | 10.5 | 0.501 | 15.2 |

6 mls. whole blood (see Table 1) was mixed with 3 ml of 60 mM GSH, GSH-ME or GSH-DE at pH 7. After 30 min incubation at 37° C., PBM were isolated by Ficoll-Hypaque density gradient centrifugation. Cells were washed with 14 ml PBS (2–3) and lysed with 4.31% SSA/0.5 mM DTPA (400 μl). After centrifugation, the supernatants were derivatized for HPLC analysis.

TABLE 4

Thiol Levels in Human Peripheral Blood Mononuclear Cells After
Treatment with GSH Esters*
Thiol Levels (nmol/$10^6$ cells)

| Thiol Applied | Thiol Found | 7 min$^A$ | 7 min$^B$ | 45 min$^B$ | 90 min$^A$ |
|---|---|---|---|---|---|
| None (saline) | GSH | 1.66 | 1.45 | 1.16 ± 0.01 | 1.38 |
| GSH | GSH | 1.86 | 1.51 | 1.16 ± 0.06 | 1.60 |
| GSH-ME | GSH | 2.05 ± 0.08 | | 1.64 ± 0.06 | 3.45 ± 0.39 |
| | GSH-ME | 1.27 ± 0.11 | | 2.75 ± 0.19 | 7.23 ± 0.88 |
| | Total | 3.32 ± 0.19 | | 4.39 ± 0.25 | 10.7 ± 1.3 |
| GSH-DE | GSH | 3.64 ± 0.32 | | 2.82 ± 0.25 | 5.58 ± 1.05 |
| | GSH-ME | 8.34 ± 0.95 | | 14.1 ± 1.0 | 26.9 ± 5.1 |
| | GSH-DE | 0.65 ± 0.016 | | 0.320 ± 0.101 | 0.750 ± 0.141 |
| | Total | 12.1 ± 1.3 | | 17.2 ± 1.4 | 33.2 ± 6.3 |

*A and B were individual donors. Values given without S.D. are means of 2 determinations. Others are means ± S.D. for three determinations.

PBM were isolated from whole blood (see Tables 1 and 3) washed with PBS, and re-suspended in PBS. To 0.9 ml cell suspension (5–8×$10^6$ cells) was added 0.3 ml of 80 mM GSH, GSH-ME or GSH-DE at pH 7. After incubation at 37° C. for the indicated times, the cells were recovered by centrifugation, washed with 14 ml PBS (2×), and lysed by addition of 4.31% of SSA/0.5 mM DTPA and 2–3 freeze-thaw cycles. After centrifugation, supernatants were derivatized for HPLC analysis.

TABLE 5

Thiol Levels in Purified Human T-Lymphoctyes After
Treatment with GSH Esters*
Thiol Levels (nmol/$10^7$ cells)

| Thiol Applied | Thiol Found | 7 min$^A$ | 90 min$^B$ |
|---|---|---|---|
| None (saline) | GSH | 3.19 ± 0.16 | 1.23 |
| BSO | GSH | 2.39 ± 0.09 | <0.6 |
| GSH ± BSO | GSH | 2.11 ± 0.21 | 0.663 |
| | Cysteine | 0.486 ± 0.017 | |
| | Total | 2.60 ± 0.23 | |
| GSH-ME ± BSO | GSH | 3.79 ± 0.09 | 2.73 ± 0.38 |
| | GSH-ME | 2.28 ± 0.22 | 4.36 ± 0.77 |
| | Cysteine | 4.23 ± 0.28 | 8.06 ± 0.72 |
| | Total | 9.16 ± 0.76 | 15.2 ± 1.9 |
| GSH-DE ± BSO | GSH | 3.79 ± 0.09 | 1.75 ± 0.25 |
| | GSH-ME | 5.89 ± 0.43 | 10.8 ± 1.5 |
| | GSH-DE | 0.249 ± 0.029 | 2.56 ± 0.31 |
| | Cysteine | 3.67 ± 0.11 | 2.20 ± 0.27 |
| | Total | 13.6 ± 0.7 | 17.3 ± 2.3 |

*A and B were individual donors. Values given without S.D. are means of 2 determinations.

Purified T-cells were suspended in PBS. To 0.9 ml cell suspension (9×$10^6$ cells for 90 min samples and 7 min saline controls; 1.8×$10^7$ cells for remainder) was added 0.3 ml 80 mM GSH, GSH-ME or GSH-DE at pH 7. After incubation at 37° C. for the indicated times, cells were recovered and processed as described for PBM in Table 4.

Where values for cysteine are not reported, levels are <0.3 nmol/$10^7$ cells (for 7 min. samples) or <0.5 nmol/$10^7$ cells (for 90 mni. samples).

TABLE 6

Thiol Levels in Hamsters Treated with GSH Esters

| Treatment | Thiol Found | Liver μmol/g | Kidney μmol/g |
|---|---|---|---|
| None (saline) | GSH | 10.0 ± 0.50 | 2.56 ± 0.30 |
| BSO | GSH | 5.10 ± 0.51 | 1.00 ± 0.19 |
| BSO ± GSH | GSH | 4.75 ± 0.06 | 1.45 ± 0.25 |
| BSO ± GSH-ME | GSH | 5.06 ± 0.36 | 2.65 ± 0.64 |
| | GSH-ME | 0.49 ± 0.10 | 2.46 ± 0.78 |
| BSO ± GSH-DE | GSH | 13.2 ± 1.71 | 2.32 ± 0.83 |
| | GSH-ME | 1.20 ± 0.28 | 1.49 ± 0.50 |
| | GSH-DE | 0.168 ± 0.008 | 0.306 ± 0.064 |

BSO (6 mmol/kg) was given I.P. fasted animals 2 hours prior to giving GSH, GSH-ME, or GSH-DE (5 mmol/kg); values were determined 1 hour later. Blood plasma levels of GSH were not affected by giving GSH-ME or GSH-DE. Each value represents determinations ±S.D. on 3–4 animals.

In view of the presently demonstrated findings set forth above and the clear correlations between the diesters of the present invention, the monoesters of the prior art, the findings disclosed herein further indicate that the administered glutathione ester is transported into the cell of the liver and kidney where it is hydrolyzed to glutathione. Prior GSH monoester studies in which mice were pretreated with buthionine sulfoximine provide strong evidence for transport of the glutathione esters; under these conditions, the synthesis of glutathione from its constituent amino acids is markedly inhibited because buthionine sulfoximine inhibits one enzyme that catalyzes the first step of glutathione synthesis.

It also seen that intact glutathione is not delivered into the cell, since glutathione synthesis is markedly inhibited by buthionine sulfoximine. Thus, the present method permits increasing the intracellular glutathione level in instances where a deficiency of the necessary synthetases for glutathione exist.

It is to be understood that the invention is not limited to the particular details described, for obvious modifications will occur to a person skilled in the art.

In addition, the esters of the present invention could be employed as safeners for plant crops by being administered thereto or to seeds prior to planting through absorbable liquid applications to protect the plants against the effects of herbicides being applied to combat weeds which are or might grow among the plant crops.

Variations of the invention will be apparent to the skilled artisan.

ABBREVIATIONS

GSH=gluthione
DNA=deoxyribonucleic acid
GSH-ME=glutathione monoethyl (glycyl) ester
GSH-DE=glutathione diethyl ester
RBC=red blood cells (erythrocytes)
PBM=peripheral blood mononuclear cells
DTT=dithiothreitol
PBS=phosphate buffered saline
DTNB=5,5'-dithio-bis-(2-nitrobenzoic acid)
EDTA=ethylene diamine tetraacetic acid
DTBA=ethylene triamine pentaacetic acid
SSA=5-sulfasalicyclic acid
mBBR=monobromobimane
Tris=tris(hydroxymethyl) amino methane
HPDL=high performance liquid chromatography
MeOH=methanol
ODS=trade name of HPLC column
BSO=L-buthionine sulfoximine
FAB=fast atom bombardment
$^1$H NMR=proton nuclear magnetic resonance
TSP=3-(trimethyl silyl) propionic 2,2,3,3,-$d_4$ acid
WBC=white blood cells (PBM)
LDL=low density lipoproteins

We claim:

1. A method for increasing levels of glutathione in a cell of a human, comprising administering to said human a glutathione dialkyl $C_2$ to $C_{10}$ ester in an amount such that said ester is transported into the cell and hydrolyzed intracellularly to glutathione.

2. The method of claim 1 wherein said glutathione dialkyl ester is at least 95% pure.

3. The method of claim 2 wherein said glutathione dialkyl ester is a diethyl ester.

4. The method of claim 3 wherein the cell is a liver cell.

5. The method of claim 3 wherein the cell is a kidney cell.

6. The method of claim 3 wherein the cell is an erythrocyte.

7. The method of claim 3 wherein the cell is a leukocyte.

8. The method of claim 7 wherein the leukocyte is a T-lymphocyte.

* * * * *